US012094359B2

(12) United States Patent
Einarsdottir et al.

(10) Patent No.: US 12,094,359 B2
(45) Date of Patent: Sep. 17, 2024

(54) SOFT BODY HAPTICS MATERIAL ARRANGEMENTS

(71) Applicant: Virtamed AG, Schlieren (CH)

(72) Inventors: Gudrun Kristin Einarsdottir, Schlieren (CH); Erika Beudeker, Schlieren (CH); Daniel Jiroudek, Schlieren (CH)

(73) Assignee: Virtamed AG, Schlieren (CH)

( * ) Notice: Subject to any disclaimer, the term of this patent is extended or adjusted under 35 U.S.C. 154(b) by 1013 days.

(21) Appl. No.: 17/012,630

(22) Filed: Sep. 4, 2020

(65) Prior Publication Data

US 2021/0074182 A1 Mar. 11, 2021

(30) Foreign Application Priority Data

Sep. 6, 2019 (EP) ..................................... 19196014

(51) Int. Cl.
*G09B 23/30* (2006.01)
*A61B 34/00* (2016.01)
*A61B 34/10* (2016.01)
*G06F 3/01* (2006.01)

(52) U.S. Cl.
CPC .............. *G09B 23/30* (2013.01); *A61B 34/10* (2016.02); *A61B 34/25* (2016.02); *G06F 3/016* (2013.01)

(58) Field of Classification Search
CPC ..................................................... G09B 23/30
USPC ......................................................... 434/267
See application file for complete search history.

(56) References Cited

U.S. PATENT DOCUMENTS

| 5,775,916 A * | 7/1998 | Cooper ................... G09B 23/28 434/272 |
| 8,992,230 B2 | 3/2015 | Tuchschmid et al. |
| 9,330,502 B2 | 5/2016 | Tuchschmid et al. |
| (Continued) |

FOREIGN PATENT DOCUMENTS

EP 3 696 794 8/2020

OTHER PUBLICATIONS

"What is Spandex?" www.fulgar.com, https://web.archive.org/web/20171230093340/http://www.fulgar.com:80/eng/insights/what-is-spandex, Dec. 30, 2017 (Year: 2017).*

*Primary Examiner* — Peter S Vasat
*Assistant Examiner* — Jennifer L Korb
(74) *Attorney, Agent, or Firm* — DLA Piper LLP (US)

(57) ABSTRACT

Anatomy mannequins, models and medical simulation systems may facilitate training by rendering a realistic tactile feedback when the end user manipulates the anatomy model with a handheld tool. An anatomy model may comprise various inexpensive material arrangements to replicate the side-to-side motion friction and resistance against the insertion and manipulation of a surgical instrument in a living body soft body tissue, such as muscle or ligament layers, while ensuring sustainability of the corresponding simulator parts over at least thousands of training sessions. A mesh layer may be arranged as an interlinked mesh of elastomer strands. A soft body layer may also be arranged as a grid of flexible protruding elements. The instrument may be inserted and manipulated through the crossings of the interlinked elastomer strands and/or the recesses or channels between the flexible protruding elements to provide a tactile feedback similar to that of real surgery tool handheld manipulation.

13 Claims, 10 Drawing Sheets

(56) References Cited

U.S. PATENT DOCUMENTS

2009/0068627 A1* 3/2009 Toly ............... G09B 23/28
                                                434/267
2017/0287361 A1* 10/2017 Caron ............. G09B 23/28

* cited by examiner

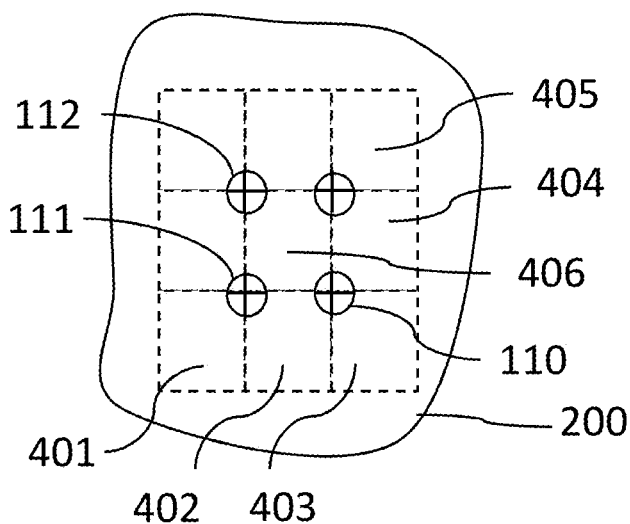
FIG. 6A
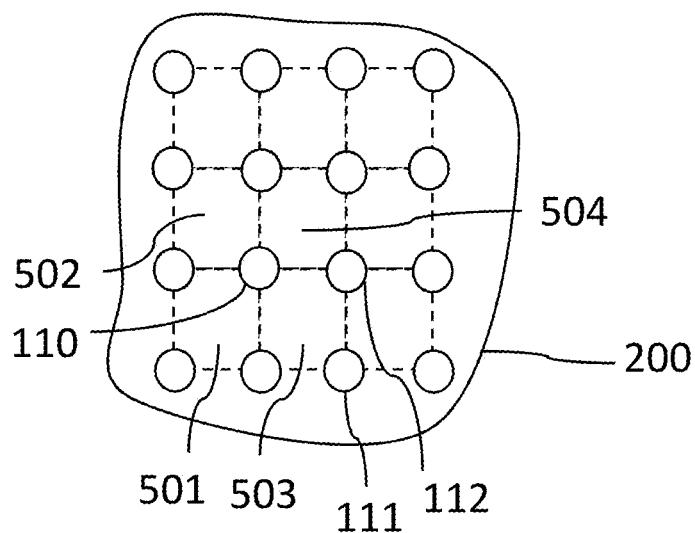
FIG. 6B
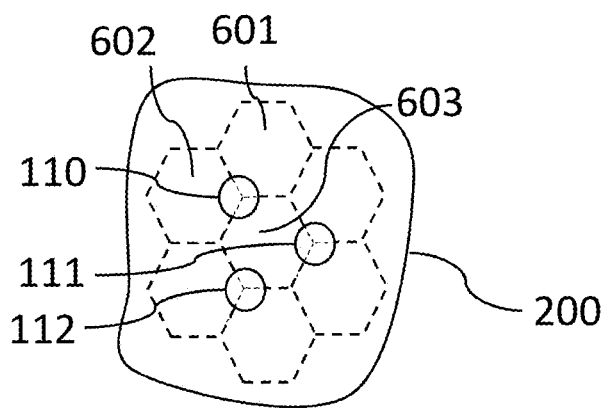
FIG. 6C
FIG. 6

SOFT BODY HAPTICS MATERIAL ARRANGEMENTS

CROSS REFERENCE TO RELATED APPLICATIONS

This application is a claims priority from European Patent Application No. 19196014.5 filed Sep. 6, 2019, which is incorporated herein by reference in its entirety.

FIELD

The present invention relates to anatomy models in general, and more specifically to anatomical soft body material arrangements for medical or surgical simulation purposes.

BACKGROUND

Medical Simulation

Medical imaging has become more and more used for both diagnostic/examination and therapeutic purposes in a number of medical applications, such as endoscopy for surgery, or ultrasound imaging for various gynecology and/or obstetrics applications. These new techniques may require dedicated training for physicians and surgeons to master the indirect hand-eye coordination required by the imaging system as well as the manipulation of the imaging tools, such as the endoscope or the ultrasound probe, in addition to the conventional medical instruments and procedures for a diversity of patient anatomies as may be encountered in medical practice. Computerized medical procedure training simulators may enable the physicians and trainees to develop and improve their practice in a virtual reality environment before actually practicing in the operation room.

Advanced medical procedure simulators may be based on a virtual reality ("VR") and/or a mixed or augmented reality ("AR") simulation apparatus by which the physician can experiment a medical procedure scenario. The VR/AR system may compute and display a visual VR/AR model of anatomical structures in accordance with physician gestures and actions to provide various feedback, such as visual feedback. In a VR system, an entire image may be simulated for display to a user, and in an AR system, a simulated image may be overlaid or otherwise incorporated with an actual image for display to a user. Various patient models with different pathologies can be selected. Therefore, natural variations as encountered over the years by practicing doctors can be simulated for a user over a compressed period of time for training purposes. The medical simulation procedure can be recorded and rehearsed for evaluation purpose. The VR/AR simulation system can also compute and provide various metrics and statistics.

VR/AR simulation systems such as the one described in U.S. Pat. No. 8,992,230 include a human anatomy model in real size. The VR/AR simulation system may further comprise a medical instrument to be handheld by the user to more realistically simulate the medical procedure. A passive feedback VR/AR simulation system such as for instance the one described in U.S. Pat. No. 8,992,230 may also be used with a diversity of medical procedure training scenarios, some of which may possibly result in a mismatch between an anatomy model surface as touched by the trainee and a virtual environment surface as computed by the VR/AR simulation system and rendered on the screen. In order to further improve the passive haptic experience and increase the realism in such medical training scenarios, the VR/AR simulation system may be further adapted with space warping methods and systems as described in U.S. Pat. No. 9,330,502.

Simulator Systems

For VR/AR medical simulators, maximizing the realism of interacting with the physical anatomy model (mannequin) with medical tools or instruments directly adapted from the real medical practice may further improve the learning experience. In many medical or surgical procedures, the user manipulates an instrument inside the patient body by inserting it through a body portal and positioning, orienting and manipulating it according the actual procedures. The portal may be a natural orifice or a surgical cut through the skin. For instance, in laparoscopy procedures, the portals are cut at predefined positions over the abdomen, while in arthroscopy procedures the portals are cut at predefined places around the joint. In real medical practice, a diversity of internal materials may be encountered, each creating a different tactile effect for the end user to perceive. It is important to properly simulate the material properties in training scenarios as bad handling can result in possible cartilage and/or internal organ damage.

In order to improve the realism of the training simulator, it is therefore desirable to reproduce this tactile perception with material arrangements reproducing the haptic feedback to be perceived by the end user when he/she is manipulating the tool within the simulator anatomical model. In particular the following problems have to be solved:

- when the tool enters into the material at a certain angle, it should not be able to freely move around as its movement would normally be limited by the surrounding tissue. It should rather feel like it is driven into the entry direction. There is thus a need to mimic the side to side motion resistance of the soft body structure against the manipulation of the tool inside the body, while still providing a realistic simulation of the body entry portal as a pivot point for the tool manipulation.
- when the tool interacts with the material, it may be preferable not to damage it—i.e. the material needs to exhibit enough resistance and a guiding force from the materials pushing back while being robust enough to sustain thousands of manipulations without the need to replace this part in the simulator.
- a solution made of off-the-shelf, inexpensive materials and manufacturing methods (cost of material as well as cost of assembly/manufacturing the solution) has to be preferred.
- the solution should preferably be stable enough not to require too frequent maintenance such as mechanical recalibration (e.g. robotic arrangement).

In an exemplary shoulder arthroscopy procedure as may be simulated with the prior art training simulator of FIG. 1, the user manipulates a surgical tool 10 by introducing it through a portal hole 110 and positioning and orienting it within the joint anatomy model 20 to manipulate the joint inner materials in accordance with the specific needs of the medical procedure to be taught to the user. Examples of tools are a probe, a hook, a punch, a grasper, a shaver, imaging tools such as endoscopes or arthroscopes, or more generally any instrument which may interact with the soft body materials inside the joint as required in medical or surgical practice. As shown on the simulated image of the joint inner structures in FIG. 1, the joint comprises a diversity of soft body structures such as muscle layers 30, ligament and tendon layers 40, as well as hard body structures such as cartilage or bones 50. Commercially available anatomy models which use rubber and plastic for all elements of the anatomy suffer from the lack of realism when manipulating the tool. While rigid plastic enables to simulate the contact with hard surfaces such as bones, rubber can only simulate certain flexible materials with limited realism. More generally, to provide a realistic haptic feedback when manipulating a tool 10 passing through a soft body element such as a muscle layer 30 or a ligament layer 40 or a combination thereof, some level of side to side motion resistance and friction needs to be simulated with the extra challenge of not degrading the muscle or ligament simulation material.

Preferably, the simulator arrangements may be manufactured with low-cost materials. It is also desirable that the material arrangements are robust enough not to require too frequent replacement of internal disposable parts, so as to facilitate the maintenance and operation of the simulator at the training facilities.

There is therefore a need for novel material arrangements which facilitate realistic tactile feedback when manipulating tools in contact with the anatomy model for a diversity of medical simulation applications without requiring an expensive material design and/or cumbersome disposable material parts replacement after manipulating the simulator.

BRIEF SUMMARY

In the frame of the current description, it is proposed an anatomy model comprising a mesh layer through which a medical tool may be inserted and manipulated into the model, the mesh layer characterized in that it is formed of at least two elastomer strands, each strand having a width in the range of 1 mm to 10 mm, the strands being interlinked so as to provide multiple gaps at the crossing of the strands through which the tool can pass through the mesh layer.

BRIEF DESCRIPTION OF THE DRAWINGS

FIG. 6A, FIG. 6B and FIG. 6C respectively show the top views for three different exemplary geometries for the soft body simulation layer to be arranged below a skin layer with a polyon-shaped grid of portal entries: FIG. 6A adjacent square foam fingers, FIG. 6B molded silicone fingers, FIG. 6C adjacent hexagonal foam fingers.

DETAILED DESCRIPTION

Mesh Layer

Figure 1:
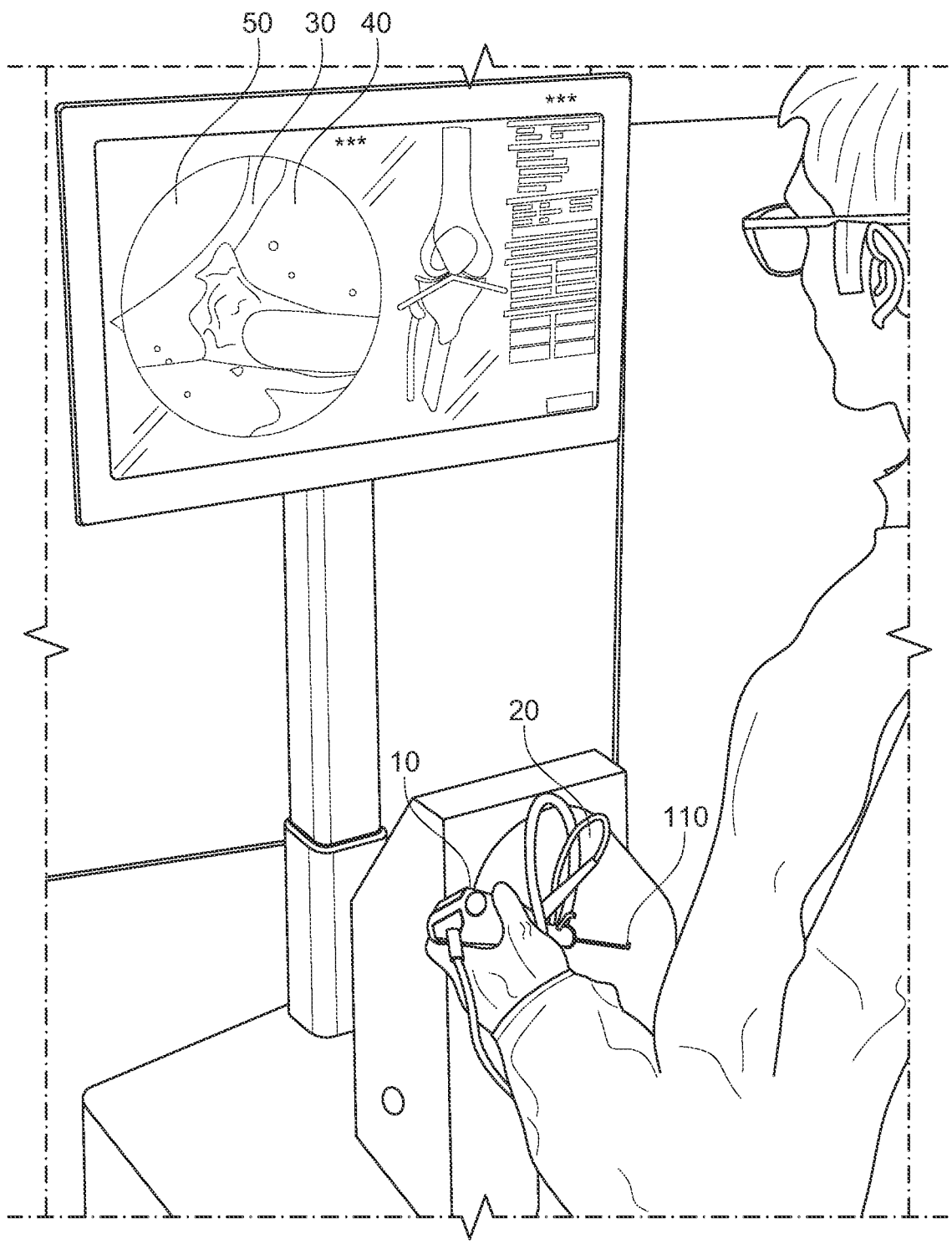
FIG. 1 illustrates an exemplary medical procedure simulator of the prior art, comprising a mannequin structure, an anatomy model such as the shoulder joint model, a tool such as the arthroscope which is inserted and manipulated by the user into the anatomy model, and a VR/AR simulator screen to display the on-going surgical procedure.
Figure 2:
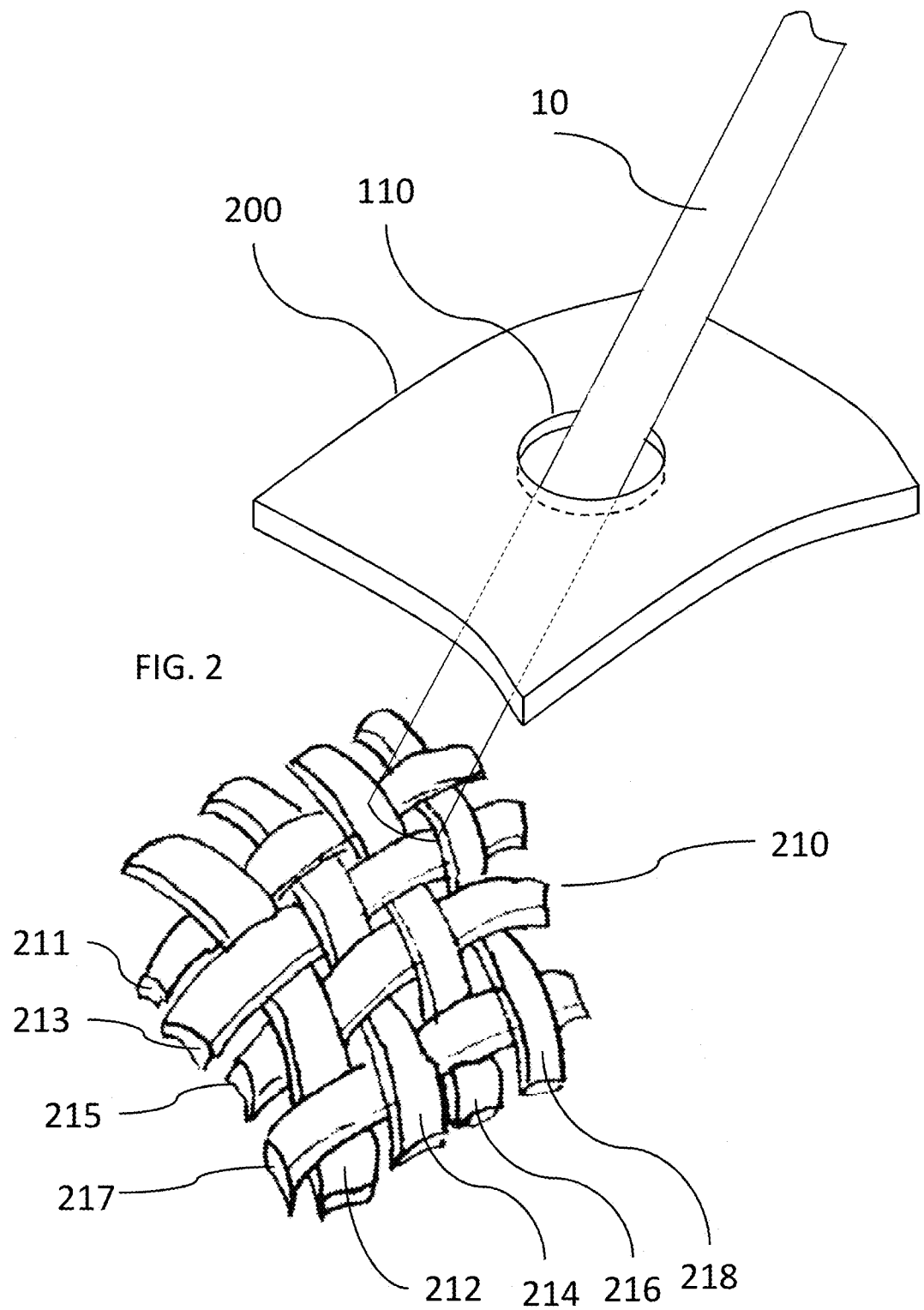
FIG. 2 provides an abstract, partial view of a possible embodiment of the proposed anatomy model simulator comprising a skin layer with a portal entry and a primary mesh layer through which the user may manipulate a tool.

FIG. 2 shows a partial abstract view of a proposed material arrangement for a mesh layer 210 which is attached to the anatomy model 20 (not illustrated) to replicate the side-to-side motion resistance and friction tactile feedback as would be perceived by the user from the interaction of a tool with a living body tissue. Preferably, the mesh layer 210 may be made of at least two strands of an inexpensive elastomer material, the one strand being interlinked with another strand so that multiple gaps are formed at the crossing of the strands through which the tool may be inserted and manipulated. In a possible embodiment, a set of three or more strands 211, 212, 213 may be interlaced or intertwined to form the mesh layer 210. The tool 10 may accordingly be inserted and manipulated into the anatomy model 20 through the gaps at the crossing of strands in the mesh 210 of interlinked strands 211, 212, 213. By using a flexible, resistant material layer, e.g. elastomer, for the strands 211, 212, 213 it is possible to address both requirements of realistic side to side motion resistance and robustness against the tool insertion regardless of its actual insertion angle.

It is to be noted that the strands do not need to be physically distinct but can be formed from a single strand in which a first section plays the role of the first strand and a second section plays the role of the second strand. The same is applicable for three or four strands.

Various elastomer materials may be used for manufacturing the strands 211, 212, 213 such as natural rubbers, styrene-butadiene block copolymers, polyisoprene, polybutadiene, ethylene propylene rubber, ethylene propylene diene rubber, silicone elastomers, fluoroelastomers, polyurethane elastomers, nitrile rubbers, or other materials with elastomer properties. A combination of different materials may also be used for different strands depending on their position relative to the joint, for instance to simulate different resistance corresponding to different anatomy areas below various portals 110, below the joint 20 skin layer 200, or to simulate different pathologies causing a different perceived touch feeling when manipulating the instrument 10 through the portal 110.

The size of the strands and/or the geometry of the mesh may also be adapted according to the properties of the joint to be simulated. Preferably, for each possible portal hole 110 on the skin, the interlinked mesh 210 may be arranged to provide multiple gaps at the crossing of strands under the skin portal hole 110 through which the tool 10 may cross the mesh layer 210. Thus, depending on the actual angle of insertion for the tool 10, a different tactile feedback may be perceived by the end user such as an increased resistance and/or friction for larger inclinations.

In general, some elasticity is needed to ease the puncture by the tool while easily recovering the initial mesh shape after manipulation, but some resistance is also needed to realistically simulate the friction of the anatomy tissue to be simulated. Different materials and/or different patterns may thus simulate different properties of anatomy tissues such as the skin (which feels harder to puncture) or fat (which feels softer to puncture).

Figure 3A:
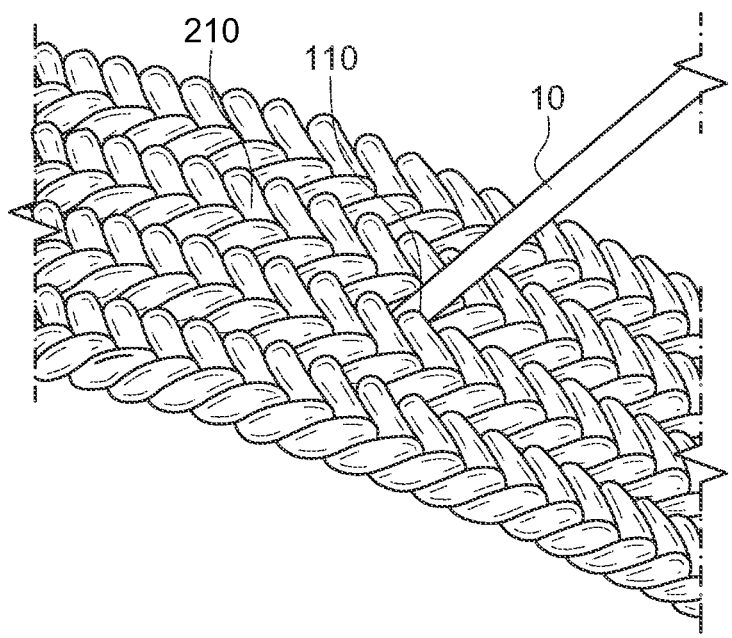
FIG. 3A, FIG. 3B, FIG. 3C and FIG. 3D show different examples of patterns of interlinked strands suitable to form a mesh layer with which a tool may interact.
Figure 3B:
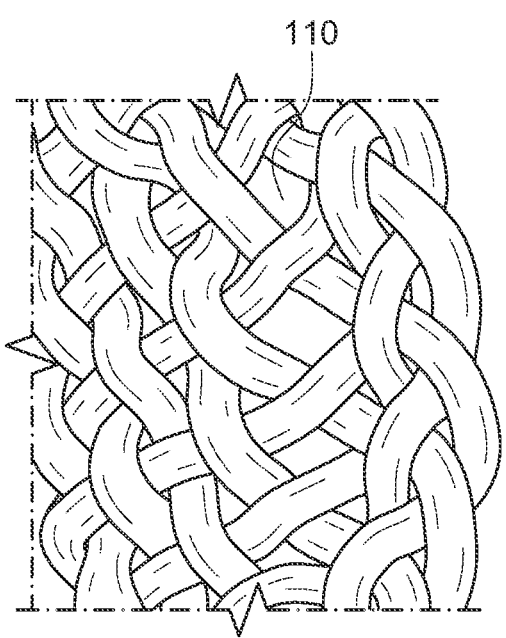
Figure 3C:
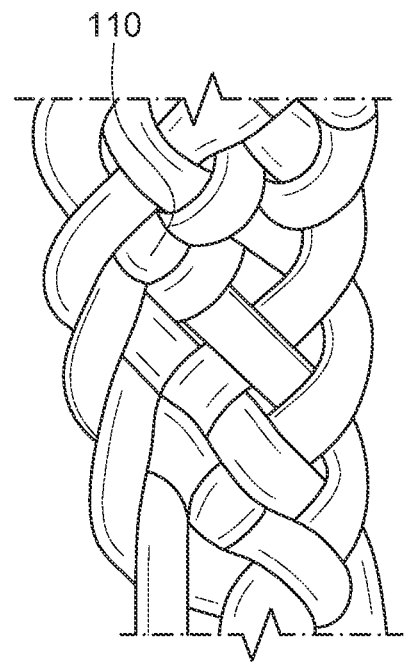
Figure 3D:
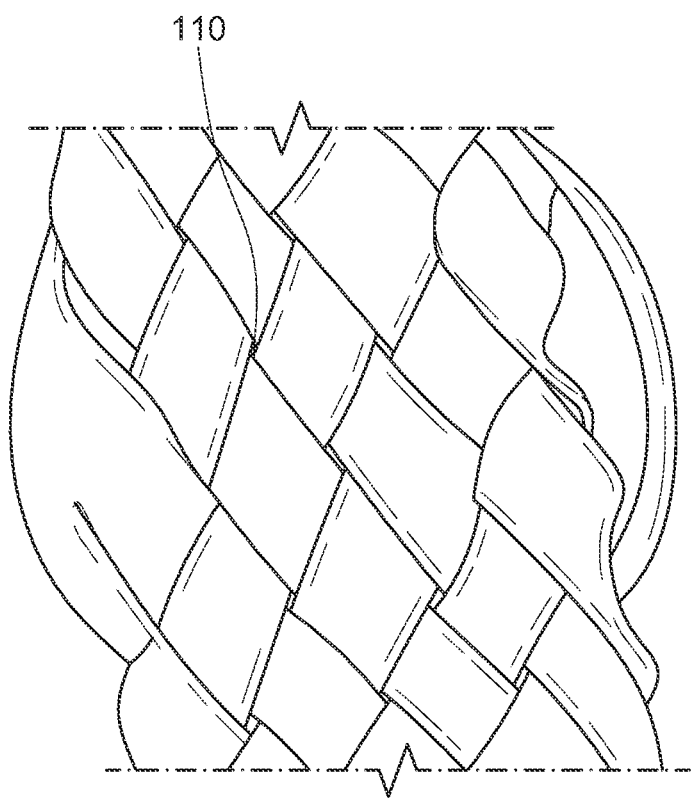

As illustrated in the examples of FIG. 2 or FIG. 3A, various geometrical patterns may be used to form the interlinked mesh 210, for instance by weaving, braiding or plaiting (as illustrated in FIG. 2 or FIG. 3A, knitting, or crocheting to form the interlinked mesh of strands 210. Different strands shapes may be used, for instance FIG. 3B, FIG. 3C and FIG. 3D respectively show the use of a circular shaped strand, an elliptical shape strand, or a rectangular shape strand. The pattern may be adapted to the diameter of the tool 10 to be inserted into the mesh layer 210. In our experiments, for conventional surgery instruments of diameters ranging from 2 mm to 6 mm, strands of width 1 to 10 mm may used. The pattern may also be adapted to the geometry of the anatomy model. In a possible embodiment suitable for an arthroscopy simulator such as the one described in co-pending European patent application EP19157591.9, a braided mesh may be attached by its two ends to two different bones in the joint model. In the case that these two strands are formed from a single folded strand, the two ends are located at one side of the mesh and attached to the bone. The other end of the mesh is also attached to the bone, where the fold of the single strand is located. In an alternate embodiment suitable for a laparoscopy simulator, a first interlinked mesh may be attached under a primary portal 110 dedicated to inflation and laparoscopy trocar insertion right under the skin of the belly anatomy model, while a second interlinked mesh may be attached at a deeper position, below the length of the trocar, within the abdominal model under the secondary portals through which one or more manipulation tools are inserted according to the laparoscopy procedures. The meshes may also be manufactured with different elasticity properties to replicate different haptic feedbacks perceived by the end user when punching the belly for initial inflation trocar insertion versus passing the tools through the muscle layers of internal organs. In the case of a joint shoulder model, some tension for the mesh is desirable to provide a realistic "popping" feeling, along with providing a pivot point at a realistic place. In our experiments, a tight mesh pattern of elastic rectangular strands forming small gaps as shown in FIG. 3D provides good results, but other embodiments are also possible.

The anatomy model 20 parts, including the skin layer 200, may be made of plastic, silicon, rubber, polyurethane, or any other suitable material. In general, the anatomy model parts are made of a flexible material, such as flexible plastic, so that it can deform under pressure. The clinical shoulder arthroscopy simulator model CLA 15 product by Coburger Lehrmittelanstalt (product information: https://cla.de/de/medizinische-uebungsphantome/arthroskopie/modelle/arthroskopie-modell-vom-schultergelenk-cla-15?number=IDS-609) may be used as the anatomy model 20, but other anatomy models may apply as well, including models for the belly, the hip, the knee, the ankle, the wrist, or the elbow.

In a possible embodiment, as illustrated by FIG. 3A, the end user may directly interact with the mesh layer 210 attached to the anatomy model 20. The mesh layer 210 may be attached to the anatomy model 20 by gluing and/or screwing both ends of each of the strands to the anatomy model 20. As will be apparent to those skilled in medical practice, such a simple arrangement may facilitate the simulation of certain procedures where multiple, very closely spaced portals 110 may be chosen by the user, so that pre-punching them into the skin layer 200 may prevent the latter anatomy model part from becoming too fragile due to repeated insertions and manipulations with the instruments 10, for instance for anesthesia, angiogram, catheter insertion simulation, etc. In contrast, the proposed mesh layer 210 is inherently both flexible and resistant against such insertions and manipulations so its sole use may be preferred to its combination with a punched skin layer 200 in certain simulator arrangements.

However, for the sake of increased visual realism, it may be preferable that the mesh layer 210 remain hidden within the simulator anatomy model 20. In another possible embodiment, the mesh layer 210 may thus be attached under the skin layer 200. For instance, in a laparoscopy simulator, the mesh layer 210 may be attached under the patient belly simulation skin layer 200 to provide more realistic feedback, in particular in teaching the insertion through a portal 110 of the initial instrument which is used to inflate the belly with gas to facilitate organ visualization, access and manipulation in laparoscopy surgical procedures. In alternate embodiments, depending on the specific location of the muscle, ligament or tendon layers to be simulated under the anatomy model 20 skin layer 200, the mesh layer 210 may be attached to one or more anatomy structure such as the bones in a joint anatomy model.

The simulator system also comprises of one or more standard tools 10, such as a hook, a probe, a punch, a grasper, a shaver, an imaging tool such as an endoscope or an arthroscope, or a standard tool replicate, to operate with the anatomy model 20 in accordance with the needs of the medical or surgical procedure to be simulated. The external (visible) skin replicate layer 200 may be further arranged to form one or more holes, each hole matching a different possible body portal entry through which a tool 10 may be manipulated inside the joint model 20 in accordance with the medical or surgical procedure. As will be apparent to those skilled in the art of surgery, several tools may also be manipulated concurrently by the end user, for instance an imaging tool on the left hand and a manipulation tool on the right hand, or by two end users in laparoscopy procedures.

Soft Body Layer

In a further possible embodiment, to provide additional realism when interacting with soft body structures such as the muscle layers in particular in certain joints such as the shoulder or the hip, the mesh layer 210 may be further adapted to the anatomy model in combination with a complementary soft body simulation layer 400. The user may interact with the simulator system joint model mannequin 20 by inserting the tool 10 through a portal hole 110 punched or cut on the model skin layer 200 to reach and manipulate an inner soft body simulation layer 400 replicating, for instance, the muscle layer as found within a real body joint such as the shoulder. In a preferred embodiment, the soft body simulation layer 400 is constructed as a material arrangement comprising adjacent protruding flexible elements between which the tool may be manipulated, as shown in FIG. 4 (photograph from a prototype arrangement taken out of the actual anatomy model, so that the protruding elements are visible).

Once the skin layer 200 and the underlying soft body simulation layer 400 are adapted to the joint model, when a tool is inserted and pressed against the soft body simulation layer 400 with a certain angle, it deforms the flexible protruding elements 401, 402, 403, 404 by compressing them, so that they touch each other and become denser, thus feeding back more resistance; when the tool reaches a recess or a channel between two adjacent protruding flexible elements, for instance, between 401 and 402 or between 402 and 403 or between 403 and 404, it slides along it, thus providing the haptic feeling of both resistance and guidance. Such an arrangement therefore provides the haptic feeling of resistance when touching the denser elements and then a softer touch as the tool slides aside them. Moreover, the flexible arrangement of the soft body simulation layer 400 enables to adjust it to the manipulation and then go back to its initial shape so that it provides a sustainable solution for thousands of manipulations.

Figure 4:
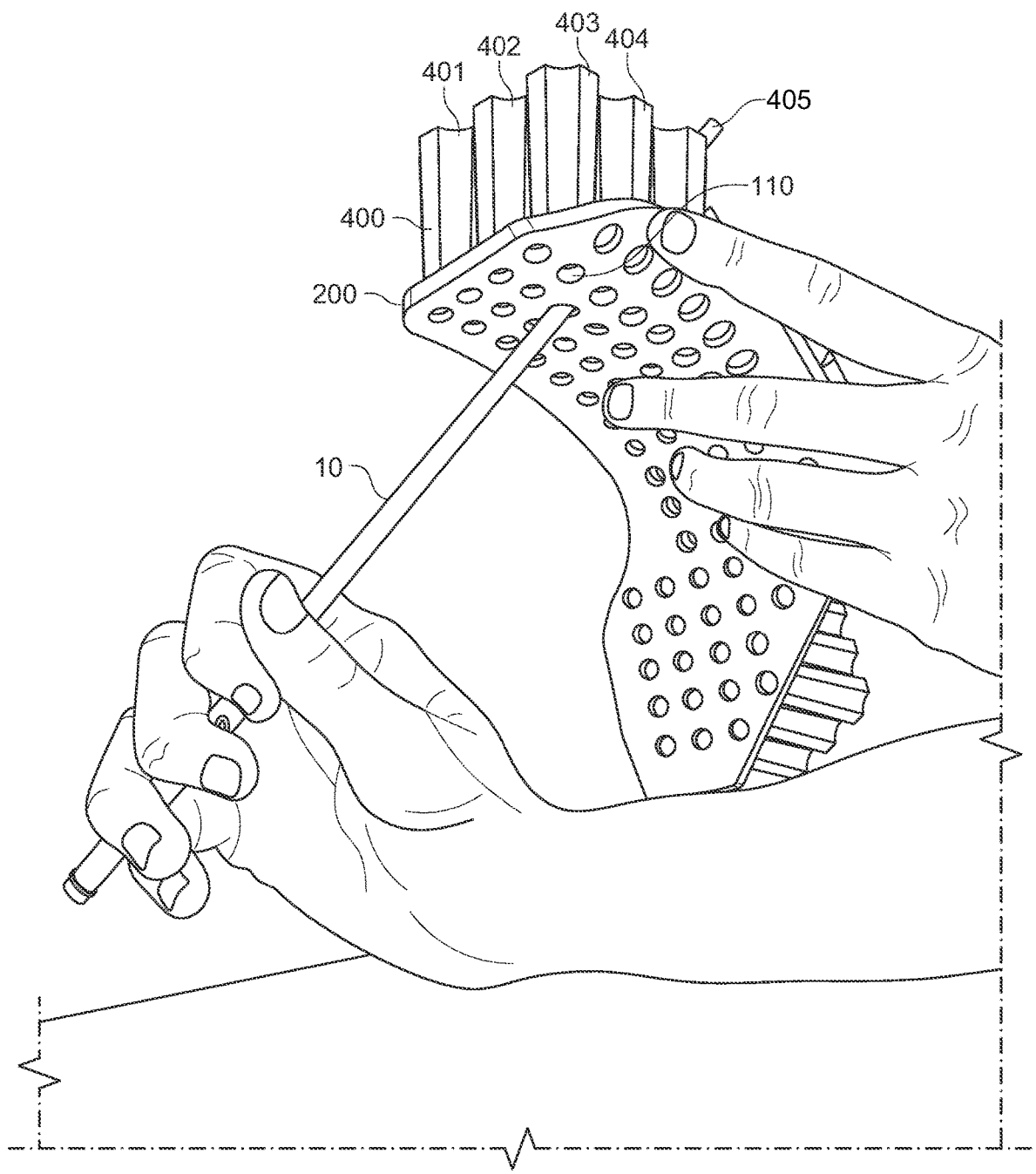
FIG. 4 is a photograph of an element of the proposed anatomy model comprising a skin layer with multiple portal entries and a secondary soft body simulation layer arranged below the skin layer (shown in an inverted bent position for the sake of illustration), through which the user may manipulate a tool.

Depending on the needs of the medical simulation and the actual simulation system, the soft body layer 400 may be attached directly to the skin layer 200, as shown in FIG. 4. In this embodiment of direct attachment to the skin layer 200, the drilled portal holes 110 may be placed each at the crossing of at least two recesses or channels separating the adjacent protruding elements (401, 402 or 402, 403 or 403, 404, etc.) on the soft body simulation layer 400.

In a possible embodiment, the material arrangement soft body simulation layer 400 may be manufactured by partially cutting adjacent protruding flexible elements through a foam material so as to form channels (partial cut lines) between the adjacent elements. FIG. 4 show such an arrangement in which the pre-cut adjacent protruding flexible elements 401, 402, 403, 404 form a soft body simulation layer of foam fingers. Preferably, a foam material of density 25 to 200 kg/m3 may be used so as to facilitate its compression within the joint anatomy model.

Figure 5A:
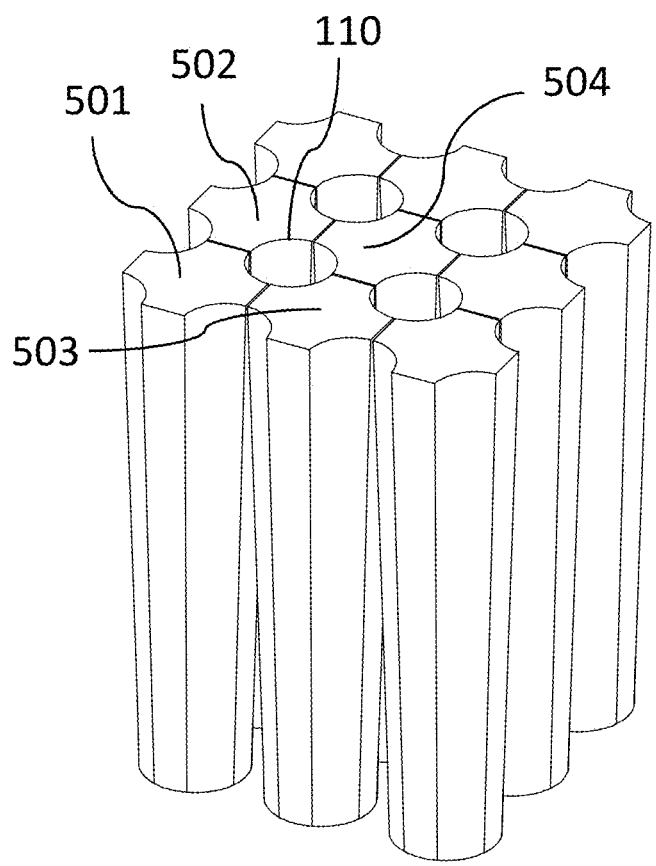
FIG. 5A and FIG. 5B show two 3D views of a possible geometry for the soft body simulation layer to be arranged below a skin layer with a square grid of portal entries.
Figure 5B:
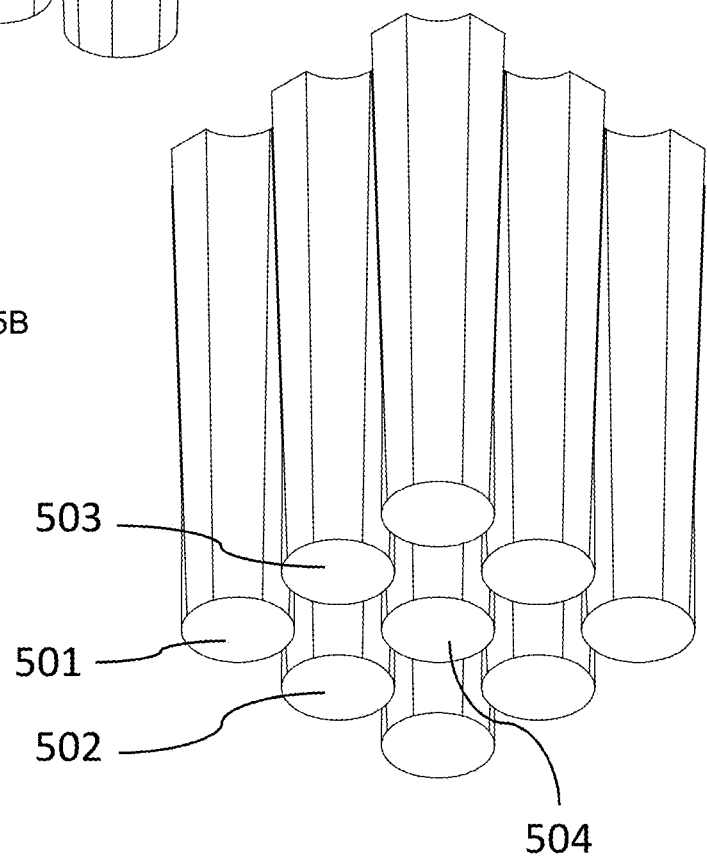

In another possible embodiment, the material arrangement soft body simulation layer 400 may be manufactured by molding the protruding elements out from a flexible material such as silicone or rubber so as to form recesses and/or channels between the adjacent elements. As illustrated in the exemplary design of FIG. 5A and FIG. 5B, the protruding elements 501, 502, 503, 504 may be molded with a cone geometry so that they can be adapted to the interior of a deformable anatomy model 20 of irregular shape, such as a joint model, where the external skin layer 200 takes a larger area than the inner space into which the protruding elements have to fit. In a possible embodiment, the cones may be molded with a varying diameter in the range 3 mm to 15 mm, but other embodiments are also possible. Preferably, a shore hardness in the range 5 to 20 Shore A may be used so as to facilitate its compression within the joint anatomy model.

The resulting soft body simulation layer may be attached onto the skin layer 200 by various means, such as gluing or screwing. In a possible embodiment, a silicon epoxy glue may be used so that the anatomy model flexible skin layer 200 does not harden with the gluing and can still be adapted to the anatomy model structures (such as bones in a joint model) in a flexible way, taking advantage of the inherent flexibility of the soft body simulation layer 400. In another further possible embodiment, the soft body simulation layer 400 may comprise a combination of different materials and/or different geometries. For instance, instead of using the foam itself to constitute the protruding elements, dedicated elements possibly of diverse materials and shapes may be fixed on the foam layer side opposite to the tool entry to form a material grid between the grid of hole entries on the foam layer, for instance, plastic tubes, silicon cones, or other material arrangements.

The protruding elements 401, 402, 403, 404 or 501, 502, 503, 504 may be arranged to form a square-shaped, a rectangular-shaped, a lozenge-shaped, a hexagon-shaped, or more generally a polygon-shaped regular grid, but irregular geometries may also be used. The protruding elements may be adjacent when partially cut into a foam material, or they may be spaced apart by a few millimeters to facilitate their molding manufacturing. FIG. 6A shows a top view of the skin layer 200 with a grid of portal entries 110, 111, 112 under which the pre-cut foam protruding elements have been glued to form a square-shaped grid aligned to the portal entries. FIG. 6B shows a top view of the skin layer 200 with a grid of portal entries 110, 111, 112 under which the molded silicon protruding elements of FIG. 5 have been glued to form a square-shaped grid aligned to the portal entries. FIG. 6C shows a top view of the skin layer 200 with a grid of portal entries 110, 111, 112 under which pre-cut hexagonal protruding foam elements have been glued to form a hexagonal-shaped grid aligned to a triangular arrangement of portal entries 110, 111, 112. Other embodiments are also possible. Depending on the embodiment, the portal entries may be placed at the intersection of the protruding elements, for example, at the intersections of four elements in the case of a square or rectangular or lozenge arrangement or three protruding elements in the case of a hexagonal arrangement. More generally, the protruding elements may be arranged so that their recesses or channels align to the grid of portal entries through which the instrument 10 may be inserted into the soft body layer 400, either directly through the portal entry holes 110, 111, 112 on the above skin layer 200.

Exemplary Shoulder Surgery Simulator

Figure 7A:
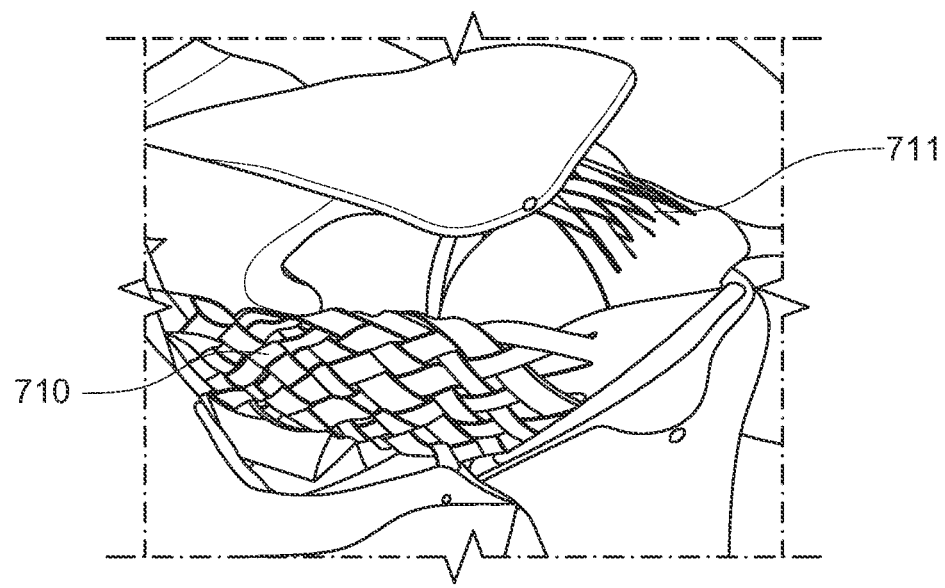
FIG. 7A and FIG. 7B different views of two separate mesh layers each attached to different bone structures, FIG. 7C inverted bent view of a soft body simulation layer made of molded silicon fingers glued to a skin layer in alignment with a square grid of portal entries and FIG. 7D external view of the joint shoulder model skin layer as seen by the end user once the skin layer has been closed over the soft body simulation layer, the bones and their associate mesh layers for simulating the internal muscle and ligament tactile feedback, FIG. 7E and FIG. 7F internal joint views of the soft body simulation layer fitting under the joint shoulder model skin layer.
Figure 7B:
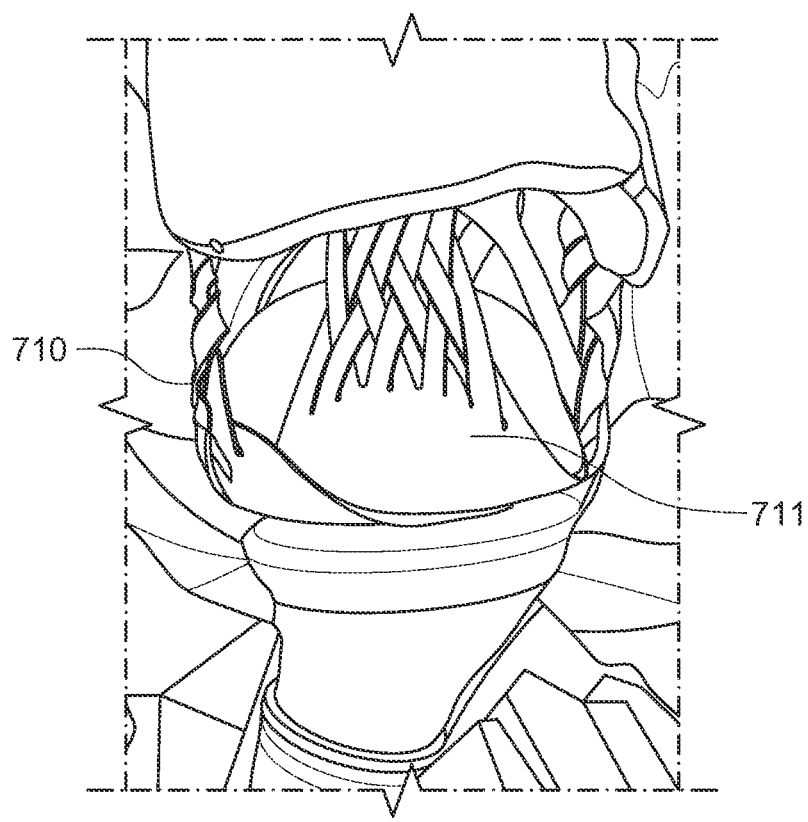
Figure 7C:
FIG. 7 provides photograph views of different parts of a prototype joint shoulder model arranged according to certain embodiments of the present disclosure.
Figure 7D:
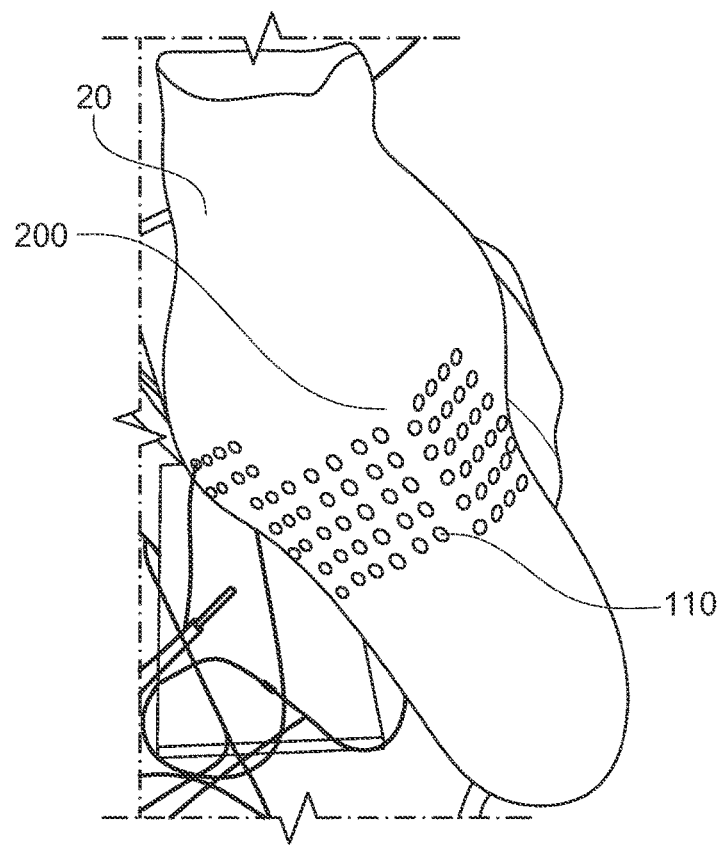
Figure 7E:
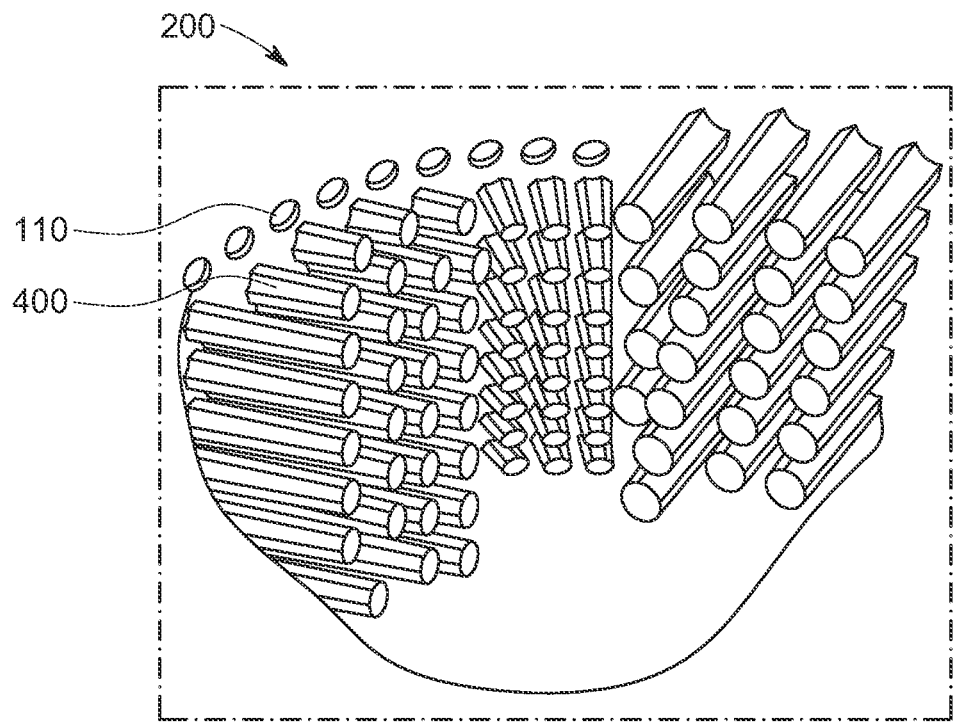
Figure 7F:
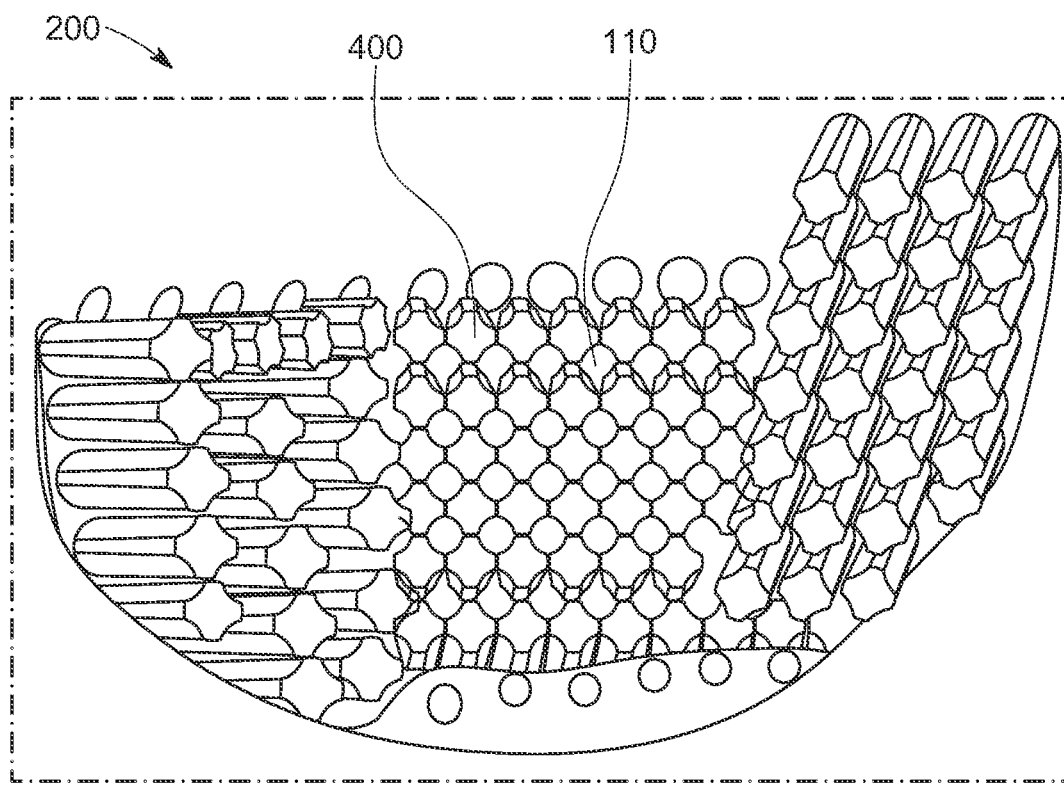

By adding any of the above described soft body layer 400 possible arrangements to prior art joint anatomy models constructs, it is possible to provide additional passive haptic feedback to further increase the tool manipulation realism similar to real practice in joint surgery, while enabling an inexpensive, robust simulator operation that will remain sustainable even after several thousands of training sessions. FIG. 7 shows different photographs of a prototype shoulder surgery simulator in accordance with certain embodiments of the present disclosure. FIG. 7A and FIG. 7B show two exemplary mesh layers 710, 711 each attached to a different bone structure in the joint model 20. FIG. 7C shows the reverse view of the soft body layer 400 arranged below the skin layer 200 (here inverted for the sake of the photograph capture). FIG. 7E and FIG. 7F show the corresponding internal joint views of the soft body simulation layer fitting under the joint shoulder model skin layer. FIG. 7D shows the external view of the simulator with multiple portal entries 110 onto the skin layer 200 of the shoulder joint model 20 for inserting and manipulating one or more medical tools through the soft body layer 400 and the mesh layers 710, 711, all those layers being hidden inside out of the view of the trainee, while providing a tactile feedback similar to real surgical manipulation of the shoulder muscles and ligaments.

As can be observed on FIG. 7E or FIG. 7F, the length of the soft body simulation layer elements (foam or silicon "fingers") may be adapted to best fit into the interior volume of the joint model. Inside the closed joint model of FIG. 7D, the interlinked mesh layer 711, 712 is placed underneath the soft body simulation layer 400, which enables to further simulate the resistance of a ligament texture against punching or cutting by some tools in certain surgical procedures to be simulated. The combination of the soft body simulation layer 400 underneath the skin layer 200 with one or more mesh layer arrangements 711, 712 over the bone structures facilitates the guidance of the tool 10 through the soft body simulation layer 400 until the tool reaches an underlying mesh layer 711, 712 (not visible in the split apart joint photograph). As illustrated on the photographs of FIG. 7A and FIG. 7B, depending on the anatomy of the joint to be simulated, multiple mesh arrangements 711, 712 may be attached to different areas of the joint bones to realistically replicate the various ligaments found into a real body joint.

Other Embodiments

While various embodiments of an anatomy tissue model have been described above, it should be understood that they have been presented by way of example and not limitation. It will be apparent to persons skilled in the relevant art(s) that the proposed models and systems can be generalized to any type of anatomy joint simulation applications, such as veterinary applications. Various changes in form and detail can be made therein without departing from the spirit and scope. In fact, after reading the above description, it will be apparent to one skilled in the relevant art(s) how to implement alternative embodiments. Thus, the present embodiments should not be limited by any of the above-described embodiments.

In addition, it should be understood that any figures which highlight the functionality and advantages are presented for example purposes only. The disclosed methodology and system are each sufficiently flexible and configurable such that they may be utilized in ways other than that shown.

Although the term "at least one" may often be used in the specification, claims and drawings, the terms "a", "an", "the", "said", etc. also signify "at least one" or "the at least one" in the specification, claims and drawings.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

What is claimed is:

1. A device comprising:
   a simulated anatomy model; and
   a mesh layer through which at least one medical tool may be inserted and manipulated attached to the anatomy model, the mesh layer being formed of at least one elastomer strand having a width in the range of 1 mm to 10 mm, the at least one strand being interlinked so as to provide multiple gaps at the crossing of the strands through which the tool can pass through the mesh layer;
   wherein the simulated anatomy model further comprises:
   a simulated skin layer comprising at least one portal hole entry through which the medical tool may be inserted and manipulated into the simulated anatomy model to reach the mesh layer; and
   a soft body simulation layer attached under the simulated skin layer, wherein the soft body simulation layer is formed of at least three adjacent protruding flexible elements such that the medical tool can enter into the soft body simulation layer through the at least one portal entry on the simulated skin layer and slide through the channels or recesses formed between the adjacent protruding flexible elements to reach the mesh layer.

2. The device of claim 1, wherein the at least one elastomer strand is formed from a material selected from the group consisting of: natural rubbers, styrene-butadiene block copolymers, polyisoprene, polybutadiene, ethylene propylene rubber, ethylene propylene diene rubber, silicone elastomers, fluoroelastomers, polyurethane elastomers, nitrile rubbers, and combinations thereof.

3. The device of claim 1, wherein the at least one elastomer strand is arranged to form an interlinked pattern in the mesh layer by weaving, braiding, knitting or crocheting.

4. The device of claim 1, wherein both ends of the at least one elastomer strand are attached to the simulated anatomy model.

5. The device of claim 4, wherein both ends of the at least one elastomer strand are attached to a bone element of the simulated anatomy model.

6. The device of claim 1, wherein at least one end of the at least one elastomer strand is attached to the simulated skin layer of the simulated anatomy model.

7. The device of claim 1, wherein the adjacent protruding flexible elements are cut in a foam material to form recesses between them.

8. The device of claim 7, wherein the foam material has a density in the range from 25 to 200 kg/m3.

9. The device of claim 1, wherein the adjacent protruding flexible elements are molded in a silicone material to form recesses and/or channels between them.

10. The device of claim 9, wherein the silicone material has a shore hardness in the range from 5 to 20 Shore A.

11. The device of claim 9, wherein the silicone protruding elements have a varying diameter from 3 mm to 15 mm.

12. The device of claim 1, wherein the adjacent protruding flexible elements are arranged as a polygon-shaped regular grid, a square-shaped grid, a rectangular-shaped grid, a lozenge-shaped grid, or a hexagon-shaped grid.

13. The device of claim 1, wherein the simulated skin layer comprises at least two portal hole entries through which one or more medical tools may be inserted and manipulated concurrently into the simulated anatomy model to reach the mesh layer.

* * * * *